(12) United States Patent
Paranjpe et al.

(10) Patent No.: US 10,443,021 B2
(45) Date of Patent: Oct. 15, 2019

(54) DEODORANT FORMULATION AND USES THEREOF

(71) Applicants: Vinay Bhalchandra Paranjpe, Dubai (AE); Donna Ruby Pancer Orense, Dubai (AE)

(72) Inventors: Vinay Bhalchandra Paranjpe, Dubai (AE); Donna Ruby Pancer Orense, Dubai (AE)

(*) Notice: Subject to any disclaimer, the term of this patent is extended or adjusted under 35 U.S.C. 154(b) by 85 days.

(21) Appl. No.: 15/669,769

(22) Filed: Aug. 4, 2017

(65) Prior Publication Data
US 2019/0040338 A1    Feb. 7, 2019

(51) Int. Cl.
| | | |
|---|---|---|
| C11D 3/48 | (2006.01) |
| C11D 3/20 | (2006.01) |
| C11D 3/00 | (2006.01) |
| A61L 9/01 | (2006.01) |
| C11D 1/94 | (2006.01) |
| C11D 11/00 | (2006.01) |
| C11D 1/66 | (2006.01) |
| C11D 1/62 | (2006.01) |
| C11D 1/90 | (2006.01) |
| C11D 1/92 | (2006.01) |
| A61L 2/18 | (2006.01) |

(52) U.S. Cl.
CPC .............. *C11D 3/2086* (2013.01); *A61L 9/01* (2013.01); *C11D 1/94* (2013.01); *C11D 3/0068* (2013.01); *C11D 3/48* (2013.01); *C11D 11/0094* (2013.01); *A61L 2/18* (2013.01); *A61L 2202/23* (2013.01); *A61L 2209/21* (2013.01); *C11D 1/62* (2013.01); *C11D 1/662* (2013.01); *C11D 1/90* (2013.01); *C11D 1/92* (2013.01)

(58) Field of Classification Search
CPC ................................ A61L 9/01; C11D 3/0068
USPC ........................................................ 424/76.1
See application file for complete search history.

(56) References Cited

U.S. PATENT DOCUMENTS

2003/0007945 A1* 1/2003 Arif .......................... A61L 9/01
                                                    424/76.1
2012/0301421 A1* 11/2012 Hecking .................. A61L 9/14
                                                    424/76.8

* cited by examiner

*Primary Examiner* — Gregory E Webb
(74) *Attorney, Agent, or Firm* — Merchant & Gould P.C.

(57) ABSTRACT

The present invention provides a stable deodorant formulation suitable for cleaning and deodorizing contaminated surfaces and areas. The deodorant formulation of the present invention comprises zinc ricinoleate, an amphoteric surfactant, a nonionic surfactant, an antimicrobial agent and water.

14 Claims, 3 Drawing Sheets

DEODORANT FORMULATION AND USES THEREOF

FIELD OF INVENTION

The present invention relates to a deodorant formulation suited for cleaning and deodorizing surfaces and areas which are contaminated with un-desired odor. In particular, the present invention relates to a deodorant composition comprising zinc ricinoleate for deodorizing surfaces and areas which are contaminated with un-desired odor.

BACKGROUND OF INVENTION

Odour emanated by surface and areas used for storing and transporting odoriferous substance leave particular odour which is difficult to remove. For marine produce specially fish particularly transported through containerized cargo, odour is formed by the bacterial action on the skin remnants on the surface used for the purpose. The surface especially of the container of the cargo needs to be freed from the odor, cleaned and disinfected prior to returning it to the shipping company.

Similarly, any surface or area in contact with marine products or any other animal products such as poultry, the remnants of which can decompose by bacterial action especially gram-positive bacteria, need to be freed from contaminants like microorganisms particularly that grow and decompose the remnants producing foul odor and the odor that has emanated by such action needs to be freed-decontaminated for the purpose of reuse.

Also, any container not associated with marine or other animal products may be required to be made odor free for various applications. For example, fragrance industries repeatedly manufacture products of different fragrance where contamination of one fragrance with another is undesired. Similarly, many cosmetic applications also require removal of smell of a previously handled product. The same applies to containers for perishable and non-perishable substances including edible products and condiments.

It is a well-known fact that solubilized zinc ricinoleate is a powerful deodorizer and there are various citations and patents that use the property of zinc ricinoleate along with various additives for the use of personal care products like anti-perspiration formulation or perspiration inhibitors. Prior art refers to various antimicrobial additives and carriers for the purpose. Many formulations include use of other zinc salts like zinc salt of abietic acid and/or other saturated or unsaturated fatty acids with 16-or more carbons, to give a synergistic effect.

US20050187124A1 discloses compositions useful for maintaining the clean impression of a carpet (that is, its scent and appearance) over an extended time despite occurrences that might damage the carpet surface. The composition, which includes an antimicrobial agent, an enzyme inhibitor, and an odor-reacting compound, can be used by a consumer to remove contaminants from the carpet and to prevent the odor associated with the decomposition of future contamination. Specifically, the composition has been shown effective in neutralizing odors associated with the decomposition of organic materials (such as urine or food spills) by absorbing and/or removing the odor-generating source. It discloses use of zinc ricinoleate as odor-absorbing compound, cationic quaternary ammonium salt as antimicrobial compound, and surfactants.

US20030199402A1 discloses a composition for reducing malodors in the air and on inanimate surfaces comprises a combination of at least one malodor neutralizing agent (eg. zinc ricinoleate), at least one malodor binding agent, at least one malodor masking agent, and at least one performance agent. In accordance with one embodiment of the invention, the composition includes a surfactant component which can be nonionic surfactants, cationic surfactants, anionic surfactants, amphoteric surfactants, zwitterionic surfactants, and mixtures thereof, a water dispersible polymer component, a metallic salt, a fragrance component, and a liquid carrier. The document also discloses that the composition may comprise a preservative which is an antimicrobial agent. This document mentions several surfactants as well as several malodor removing agents.

U.S. Pat. No. 9,302,127B2 discloses an improved deodorant formulation having good efficacy and excellent stability. The deodorant formulation comprises propanediol combined with zinc ricinoleate, grapefruit seed extract, and sodium bicarbonate as the principal deodorizing actives. The combination of these deodorizing active ingredients results in a formulation with strong efficacy which lasts at least 24 hours.

U.S. Pat. No. 8,318,806B2 discloses an odour absorbing composition is provided comprising zinc salt of ricinoleic acid, a solubility promoter including sodium iminodisuccinate, water and optionally, other ingredients such as perfumes and antifungal agents or bactericides.

US20140112602A1 discloses a novel zinc ricinoleate-containing malodor reducing composition further comprising (a) cyclohexanol, 4-isopropyl: propionate, cis; (b) cyclohexanemethanol, alpha-methyl: acetate; (c) butyric acid: 1-cyclohexylethyl ester; and (d) cyclohexanemethanol, alpha-methyl, wherein the ratio of (a):(b):(c):(d) is about 2.8-4.8:0.5-2.5:0.1-1:0.25-1, and wherein zinc ricinoleate is at a level of about 1-3% by weight.

There continues to be a need for a deodorant formulation which can clean and deodorize surfaces and areas which are contaminated with un-desired odor.

SUMMARY OF INVENTION

In one aspect of the present invention, there is provided a deodorant formulation, comprising zinc ricinoleate, an amphoteric surfactant, a nonionic surfactant, an antimicrobial agent and water.

In another aspect of the present invention, there is provided a deodorant formulation comprising zinc ricinoleate in an amount of 20% by weight, Cocoamido propyl betaine or Cocodiamido propyl hydroxyl sultaine in an amount of 10% by weight, alkyl poly glucoside in an amount of 40% by weight, alkyl dimethyl benzyl ammonium chloride in an amount of 10% by weight, and water in an amount of 20% by weight.

In another aspect of the present invention, there is provided a process for preparing the deodorant formulation, comprising the steps of: a. adding the nonionic surfactant to water at room temperature, mixing well and adding zinc ricinoleate to obtain a homogenous mixture; b. adding antimicrobial agent, and amphoteric surfactant to the homogenous mixture, to obtain the deodorant formulation.

In another aspect of the present invention, there is provided a process for preparing the deodorant formulation, comprising the steps of: a. adding the alkyl poly glucoside in an amount of 40% by weight to water in an amount of 20% by weight at room temperature, mixing well and adding zinc ricinoleate in an amount of 20% by weight to obtain a homogenous mixture; b. adding alkyl dimethyl benzyl ammonium chloride in an amount of 10% by weight, and Cocoamido propyl betaine or Cocodiamido propyl hydroxyl sultaine in an amount of 10% by weight to the homogenous mixture, to obtain the deodorant formulation.

BRIEF DESCRIPTION OF THE DRAWINGS

The present invention will now be better understood with reference to the description and to the accompanying figures.

DETAILED DESCRIPTION OF INVENTION

Figure 1A:
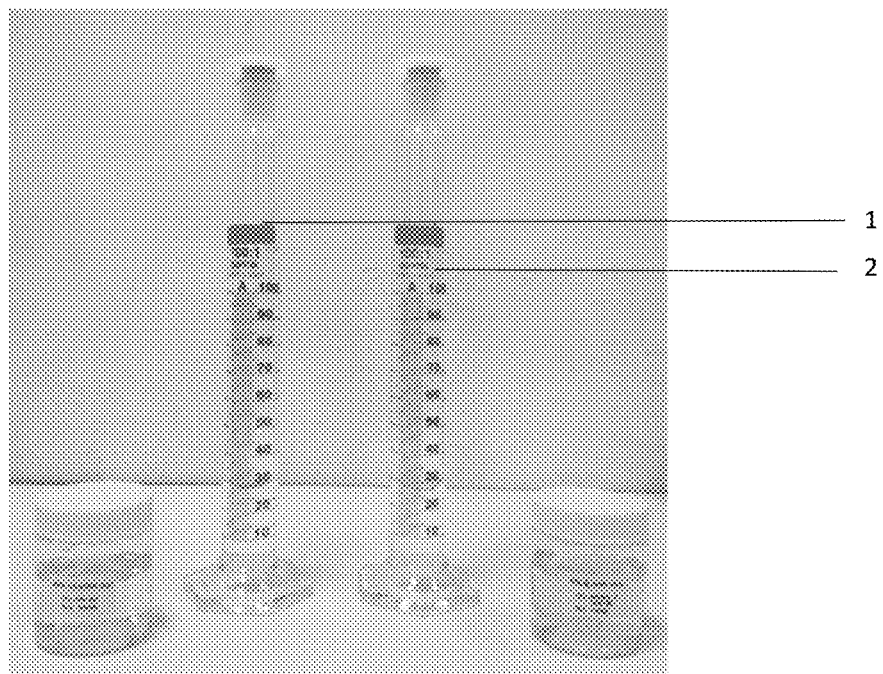
FIG. 1A illustrates the foaming of the hand wash formulations before shaking
Figure 1B:
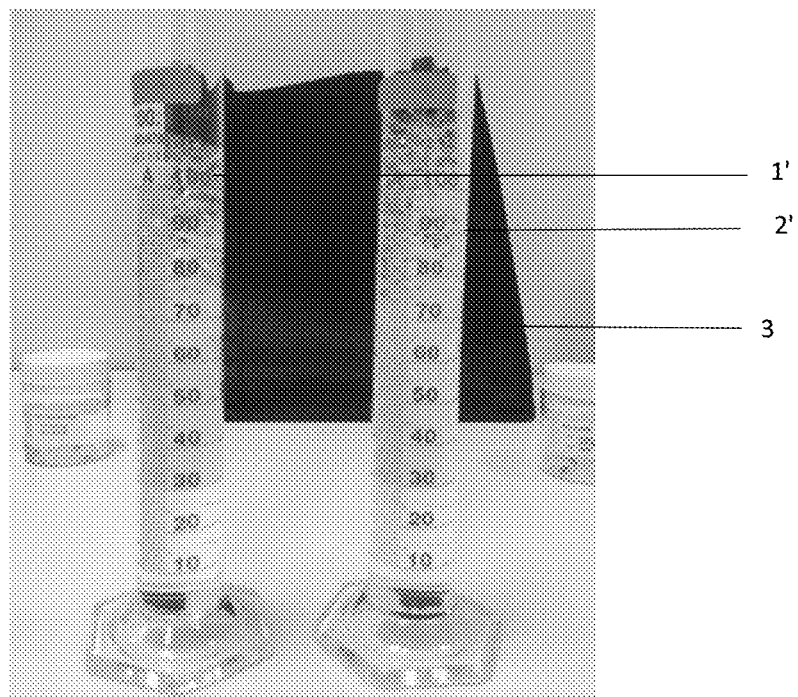
FIG. 1B illustrates the foaming of the hand wash formulations immediately after shaking
Figure 1C:
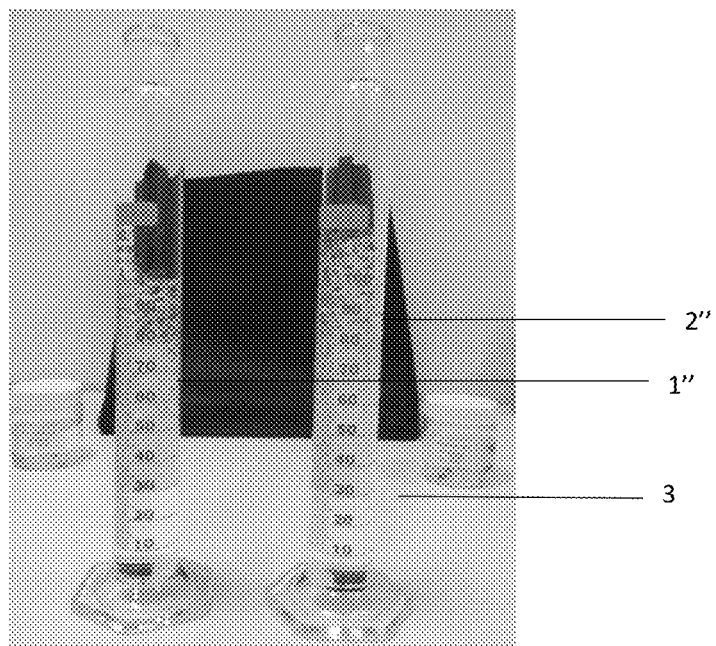
FIG. 1C illustrates the foaming of the hand wash formulations five minutes after shaking
Figure 1D:
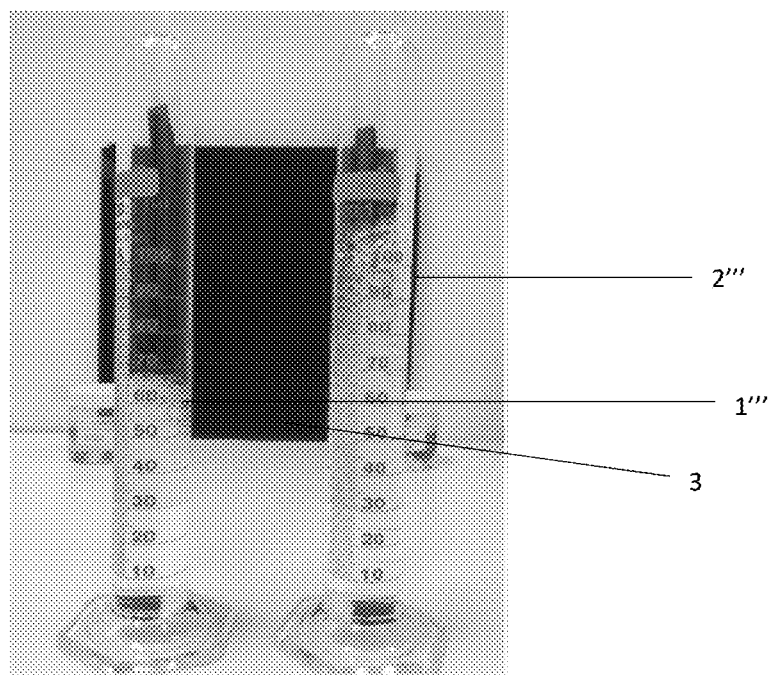
FIG. 1D illustrates the foaming of the hand wash formulations ten minutes after shaking

The present invention provides a deodorant formulation for cleaning and deodorizing surfaces and areas contaminated by un-desired odor.

The present invention describes preparation of formulation with deodorizing action which include the solubilized zinc salt of ricinoleic acid. The formulation of the present invention also comprises other components.

Zinc Ricinoleate is a salt of resinoleic acid. It is a powerful odour remover as already known in the art. Zinc Ricinoleate is often used in cosmetic application in sprays for personal deodorisers and such application but is not used in industrial material handling.

In one embodiment, the zinc ricinoleate is present in the deodorant formulation in an amount of from about 0.1 to 60% by weight based on the total weight of the formulation. In another embodiment, the zinc ricinoleate is used in the deodorant formulation in an amount of from 2 to 25% by weight, based on the total weight of the formulation. In yet another embodiment, the zinc ricinioleate is used in the deodorant formulation in an amount of 20% by weight based on the total weight of the formulation.

In addition to zinc ricinoleate, the deodorant formulation comprises a nonionic surfactant and an amphoteric surfactant. The combination of a nonionic with an amphoteric surfactant produces a synergy that dispels the need for any anionic surfactant. The synergistic effect of the combination provides a powerful cleaner which is safe as well as highly bio degradable. Thus, it eliminates the harmful and often less biodegradable anionic surfactants which are often and normally used in industrial and household cleaners.

The present invention uses non-ionic surfactant, specifically APG and an amphoteric surfactant. Though the prior art in general discloses use of surfactants which can be nonionic surfactants, cationic surfactants, anionic surfactants, amphoteric surfactants, zwitterionic surfactants, and mixtures thereof, there is no hint of using preferably non-ionic surfactant, specifically APG and an amphoteric surfactant.

In one embodiment, the nonionic surfactant is alkyl poly glucosides (APG). The alkyl poly glucosides are derived from $C_4$-$C_{18}$ alcohol, preferably $C_6$-$C_{14}$ alcohol and more preferably $C_5$-$C_{10}$ alcohol. In one embodiment the degree of polymerization of alkyl poly glucosides is from 1 to 1.6. The APG is derived from corn/potato starch and palm kernel oil. It is proven to be mild to living cells.

In one embodiment, the APG in the deodorant formulation in an amount of from about 1 to 60% by weight based on the total weight of the formulation. In another embodiment, the APG is used in the deodorant formulation in an amount of from 15 to 45% by weight, based on the total weight of the formulation. In yet another embodiment, the APG is used in the deodorant formulation in an amount of 40% by weight, based on the total weight of the formulation.

In one embodiment, the amphoteric surfactant is selected from betaines or sultaines. The betaines and sultaines are derived from coconut oil, palm oil or palm kernel oil. In one embodiment, the amphoteric surfactant is Cocoamido propyl betaine (CAPB) or Cocodiamido propyl hydroxyl sultaine (CAPHS). CAPB is an environmentally friendly surfactant which was actually created to replace Cocodiethanolamide (CDEA) and its nitrosamines threat. CAPB and CAPHS are safe surfactant and mild to living cells.

In one embodiment, the CAPB is present in the deodorant formulation in an amount of from about 1 to 25% by weight based on the total weight of the formulation. In another embodiment, the CAPB is present in the deodorant formulation in an amount of from 5 to 15% by weight, based on the total weight of the formulation. In yet another embodiment, the CAPB is present in the deodorant formulation in an amount of 10% by weight, based on the total weight of the formulation.

In one embodiment, the CAPHS is present in the deodorant formulation in an amount of from about 1 to 25% by weight based on the total weight of the formulation. In another embodiment, the CAPHS is present in the deodorant formulation in an amount of from 5 to 15% by weight, based on the total weight of the formulation. In yet another embodiment, the CAPHS is present in the deodorant formulation in an amount of 10% by weight, based on the total weight of the formulation.

In the present invention, APG is used as primary surfactant in combination with an amphoteric surfactant like CAPB/CAPHS. Normally APG is used as a secondary surfactant to other Anionic surfactants.

The deodorant formulation further comprises an antimicrobial agent. Antimicrobial agents help destroy and/or control the amount of bacteria and/or fungi present on surface to be treated. In one embodiment, the antimicrobial agents can be selected from quaternary ammonium salts such as alkyl dimethyl benzyl ammonium chloride also known as Benzalkonium Chloride (BKC), Bronolpol(2-bromo-2-nitro-1,3-propanediol) or IPBC(3-iodo-2-propenylbutylcarbamate). In one embodiment, the antimicrobial agents are quaternary ammonium salts such as alkyl dimethyl benzyl ammonium chloride also known as Benzalkonium Chloride or BKC.

BKC is a well-known disinfectant and preservative that has been used since long as a disinfectant for industry as well as in household applications. It has also been used as a preservative in pharma applications such as in nasal drops and creams for topical applications. BKC is actually a cationic surfactant and therefore is not used with cleaners which have anionic surfactants. The choice of surfactants in the present deodorant formulation allows use of BKC in a triple role. It works as a preservative, surfactant and as well as a disinfecting agent when applied to any surface that needs cleaning.

Bronopol and IPBC are safe ingredients commonly used in many cosmetics for topical applications.

In one embodiment, the BKC is present in the deodorant formulation in an amount of from about 1 to 25% by weight based on the total weight of the formulation. In another embodiment, the BKC is present in the deodorant formulation in an amount of from 5 to 15% by weight, based on the total weight of the formulation. In yet another embodiment, the BKC is present in the deodorant formulation in an amount of 10% by weight, based on the total weight of the formulation.

The present deodorant formulation further comprises water. The water used in the formulation is selected from deionized, filtered, demineralized, or alternatively tap water. The water is preferably tap water with degrees of hardness which is sufficiently low so as not to impede the effectiveness of the formulation.

In an embodiment, the water is present in the deodorant formulation in a maximum amount of 95% by weight based on the total weight of the formulation. In an embodiment, the water is present in the deodorant formulation in an amount of 20% by weight based on the total weight of the formulation.

In one embodiment, the present invention provides a deodorant formulation comprising zinc ricinioleate, Benzalkonium Chloride, alkyl poly glucosides, Cocoamido propyl betaine and water. In one embodiment, the zinc ricinioleate is present in the deodorant formulation in an amount of 20% by weight, Benzalkonium Chloride is present in the deodorant formulation in an amount of 10% by weight, CAPB is present in the deodorant formulation in an amount of 10% by weight, APG is present in the deodorant formulation in an amount of 40% by weight and water is present in the deodorant formulation in an amount of 20% by weight.

The present invention also provides a process for preparing the deodorant formulation. The formulation is prepared by mixing the components in any conventional manner, such as, for example, by simultaneous, portion wise or successive addition of components or by metered additions of some selected components.

The process for preparing the deodorant formulation, comprises the steps of: adding the nonionic surfactant to water at room temperature, mixing well and adding Zn-ricinoleate to obtain a homogenous mixture; adding antimicrobial agent, and amphoteric surfactant to the homogenous mixture, to obtain the deodorant formulation. In a preferable embodiment, the process for preparing the deodorant formulation, comprises the steps of: adding the alkyl poly glucoside in an amount of 40% by weight to water in an amount of 20% by weight at room temperature, mixing well and adding zinc ricinoleate in an amount of 20% by weight to obtain a homogenous mixture; adding alkyl dimethyl benzyl ammonium chloride in an amount of 10% by weight, and Cocoamido propyl betaine or Cocodiamido propyl hydroxyl sultaine in an amount of 10% by weight to the homogenous mixture, to obtain the deodorant formulation.

By using the selected active ingredient in combinations, a stable, deodorant formulation is prepared which do not precipitate out in aqueous solutions.

A 3-10% of the deodorant formulation was made with normal water to obtain a cleaning solution. The cleaning solution was applied to a surface at ambient temperature of 20-45 degrees C. and the retention time for the cleaning solution on the surface is 20-45 minutes depending on the intensity of the case. For the purpose of the present invention, "surface" as used herein refers to any hard surface that requires cleaning, disinfecting and to be made odor free.

The deodorant formulation of the present invention finds application in various cleaning formulation such as, in hand dishwashing detergents, all-purpose cleaners, carpet cleaners, deodorizing household cleaners, industrial cleaners, adsorbents in filters, deodorizing formulations for use in domestic and commercial animal keeping, deodorizing formulations for the treatment of textile fibers and fabrics. For the purpose of the present invention, the deodorant formulation can be applied on any hard surface.

The deodorant formulation creates an environmentally safe deodorising, disinfecting cleaner which is safe for humans and animals alike. The wash water containing this formulation can be discharged into normal sewage without any extraordinary treatment being required. It would be harmless to natural water bodies and fish alike. The formulation has the additional property of being able to save on the usage of water as the number of times the surface to be cleaned, disinfected and deodorised is reduced drastically. The excellent rinse property of the APG of short chain is very effectively used here to utmost advantage.

Experiments were conducted on site to prove the effectiveness of the deodorant formulation of the present invention. These experiments and analysis include but are not limited to the following:
1) elimination of odor in areas that require a neutral smell but have strong odor to start with
2) necessary disinfection required for food processing and environmental concern
3) cleaning of hard surfaces for proper hygiene The examples are intended to be purely exemplary of the invention and should therefore not be considered to limit the invention in any way. Efforts have been made to ensure accuracy with respect to numbers used, but some experimental errors and deviations should be accounted for.

EXAMPLES

Example 1—Hand wash Formulations

A hand wash formulation with only nonionic surfactant and a hand wash formulation with combination of nonionic surfactant and amphoteric surfactant were prepared to determine the cleaning efficiency of the surfactants. $C_{08}$ APG was taken as the nonionic surfactant and CAPB was taken as the amphoteric surfactant. A 10% solution of APG in water and 10% solution of APG and CAPB in water were prepared. The solutions were decanted in a 100 mL Graduated Cylinder up to 30 mL mark. The cylinders were closed and shook manually using the same hands at the same time. The foams/bubbles were observed at 0 seconds, 5 minutes and 10 minutes after shaking.

As seen in FIG. 1, the hand wash formulation containing both APG and CAPB shows greater foaming than the hand wash formulation containing only APG immediately after shaking. There is no change in the foam height even after 10 mins for the hand wash solution containing both APG and CAPB while the foam height reduces for the hand wash formulation containing only APG. Table 1 shows the foam height of the two hand wash formulations at different times.

TABLE 1

| Foam Properties of Hand wash Formulations | | | |
| --- | --- | --- | --- |
| Foam Properties, height in mm | 0 s | 5 min | 10 min |
| C08 APG only, 10% solution in water | 80 mm | 70 mm | 38 mm |
| C08 APG + amphoteric, 10% solution in water | 90 mm | 85 mm | 80 mm |

It is evident from FIG. 1 and Table 1 that a combination of APG and CAPB shows greater foam height than when APG is used alone in the hand wash formulation. It is known that foaming provides good assistance in dispersing soil or dirt and oils. Stability in foam increases the detergency power of the surfactant. This shows that a hand wash formulation comprising both APG and CAPB will provide better cleaning than the hand wash formulation comprising only APG.

Example 2—Preparation of the Deodorant Formulation

A deodorant formulation comprising the following ingredients is prepared:

| Components | | Amount (% by weight) |
|---|---|---|
| Solubilized zinc ricinoleate | (30% active) | 20.0 |
| Water | | 20.0 |
| BKC | (80% active) | 10.0 |
| Amphoteric surfactant | (35% active) | 10.0 |
| APG | (50% active) | 40.0 |

40% by weight of APG was added to 20% by weight water at room temperature (50%), mixed well and then 20% by weight solubilized Zn-ricinoleate was added. To this homogenous mixture, 10% by weight BKC and 10% by weight CAPB/CAPHS were added.

A 3-10% solution of deodorant formulation prepared above was made with normal water. The resulting cleaning solution was applied on a surface, which has to be cleaned and made odor free, for an application time of 20-45 minutes. Case studies were conducted to evaluate the effectiveness of the cleaning solution to eliminate the odor, to clean the hard surfaces and to disinfect the area. These were taken on different areas with different juries of a minimum of 5 people. This is a hedonistic process which consist of a jury of 5-9 people. The scale of rating is as described below in different studies. Multiple people helped smoothen out exaggerated individual opinions and give a good average understanding of the situation.

Study 1: Eliminating Odors in the Reactor/Vessels
Method

Evaluation was done where a single reactor or vessel is used for manufacturing various fragrance, for eliminating other fragrance. Thus it is required to eliminate the odor of previous product before processing the next product. The deodorant formulation of present invention was tested for eliminating the Cendol flavor. 10 ml of the deodorant formulation was added into 20 mL of water and 10% solution of the resulting 30 mL cleaning solution was used for analysis. The vessel producing the cendol flavor was washed with the above solution.

For the purpose of the study, three sets of experiment were conducted in a separating funnel, Set 1: As control, Set 2: washed with water only, Set 3: washed with the present cleaning solution. In the control the funnel was not washed with any solution and in set 2, the funnel was washed with only water. The results of washing the funnel with the present cleaning solution was compared with Set 1 and Set 2.

a) Set 1: As Control
1. 5-6 g of Cendol flavor was passed through the funnel
2. Flavor was drained b) Set 2: Washed with Water (H2O) only
1. 5-6 g of Cendol flavor was passed through the funnel
2. Flavor was drained
3. Funnel was soaked with 20 mL of water for 30 minutes
4. Water was drained
5. Funnel was soaked with 20 mL of water for 30 minutes
6. Water was drained
7. Funnel was soaked with 20 mL of water for 30 minutes
8. Water was drained c) Set 3: Washed with cleaning solution
1. 5-6 g of Cendol flavor is passed through the funnel
2. Flavor was drained
3. Funnel was soaked with 20 mL of 3.33% Cleaning Solution for 30 minutes
4. Solution was drained
5. Funnel was soaked with 20 mL of water for 30 minutes
6. Water was drained
7. Funnel was soaked with 20 mL of water for 30 minutes
8. Water was drained Results Table 2 shows the rating of smell retained on the separating funnel. According to the rating of smell, 1—poor and 5—strong. The results show that smell has been removed for Set 3 with Cleaning Solution (3.33% solution). The Set 2 still contains cendol smell after 3 rinses over water. This shows effective removal of Cendol odor in Set 3 with only one rinse.

TABLE 2

Smell retained on separating funnel

| | SET 1 As Control | SET 2 Only $H_2O$ | SET 3 With Cleaning Solution |
|---|---|---|---|
| After Flavor is drained | 5 | 5 | 5 |
| After 1st Rinse | Rinse not Done | 4 | 3 |
| After 2nd Rinse | Rinse not Done | 4 | 1 |
| After 3rd Rinse | Rinse not Done | 3 | 0 |

Table 3 shows the rating for the smell retained in the rinsed water and Cleaning Solution. According to the rating of smell, 1—poor and 5—strong. The results show that cendol smell is retained in the cleaning solution after first rinse. Less smell is retained by the water for set 3 after the second rinse.

TABLE 3

Smell retained the rinsed water and Cleaning Solution.

| | SET 1 As Control | SET 2 Only $H_2O$ | SET 3 With Cleaning Solution |
|---|---|---|---|
| After 1st Rinse | Not Performed | 5 | 5 |
| After 2nd Rinse | Not Performed | 2 | 1 |
| After 3rd Rinse | Not Performed | 0 | 0 |

Figure 2:
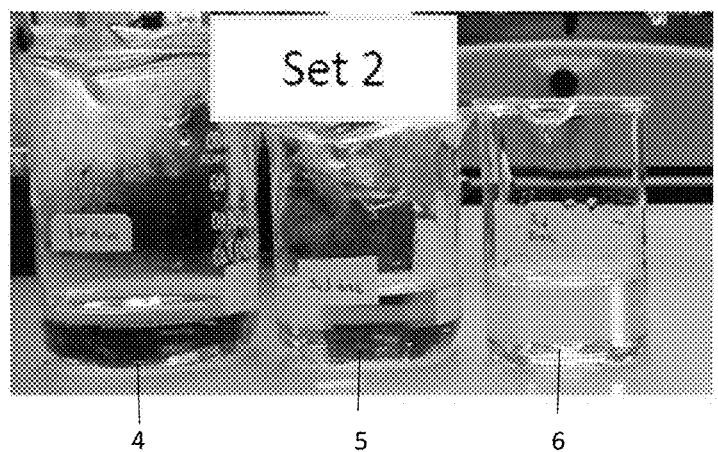
FIG. 2 illustrates the appearance of the cleaning solution and rinse water for Set 2 and 3 in Study 1.
Figure 2B:
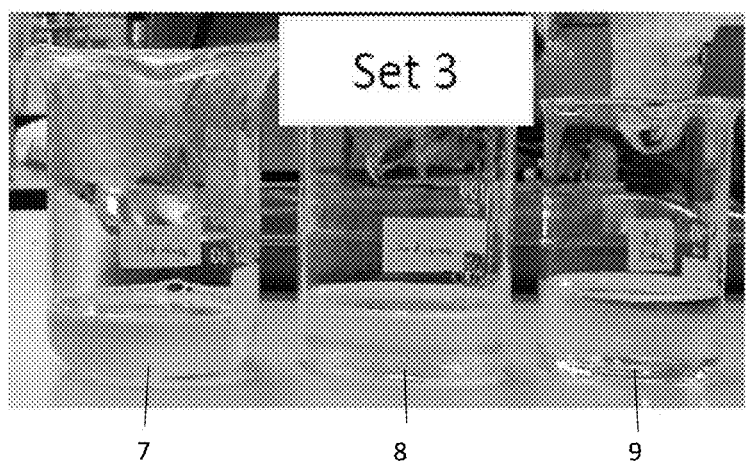

FIG. 2 shows the appearance of the cleaning solution and rinse water for Set 2 and 3. As observed in FIG. 2, the appearance of all rinsed water in Set 2 is clear. The appearance of rinsed water after 3rd rinse for Set 3 is clear. Cloudy appearance has been detected after first and second rinse. The rinsed water in Set 3 after the first rinse contains the Cendol Flavor (Brown color) which settles at the bottom of the beaker. This further shows the effective removal of the cendol smell in set 3 with only one rinse.

Study 2: Cleaning, Disinfection and Eliminating Odor in Poultry Farm

Method

Poultry farms or Hen Houses require to maintain a strict hygiene, area free of bacteria and viruses, and odorless farm. The area should be clean and disinfect regularly without affecting the health of the birds and humans involved. The deodorant formulation was tested for cleaning, disinfecting and eliminating the odor. As in Case Study 1, 3.33% of the Cleaning Solution was used for the analysis. The area tested was an indoor broiler.

For the purpose of study, experiment was performed on two areas, Area A was cleaned in a conventional manner with water, detergent and disinfectant and Area B was cleaned with the cleaning solution.

a) Area A: Cleaning, disinfecting and odor removing with a conventional product.

Area A was treated with 5-step process:
  i. Water was sprayed with a spray gun in the area.
  ii. It was followed by spraying the area with a cleaning detergent product and left for 15 minutes.
  iii. The area was rinsed with water using spray gun again.
  iv. The area was then sprayed with a liquid disinfectant and left for 30 minutes.
  v. The area was rinsed with water using spray gun.

b) Area B: Cleaning, disinfecting and odor removing with Cleaning Solution.

Area B was treated with 2-step process:
  i. Cleaning Solution 3.33% was sprayed with a spray gun in the area. The solution was retained for 15 minutes.
  ii. The area was rinsed with water using spray gun.

For cleaning and odor removing, a set of 9 volunteers acted as juries. For cleanliness, rating of 5 as the dirtiest and 0 as the cleanest. For odor, rating of 5 as the strongest and 0 as none.

Results

Table 4 shows the cleanliness achieved in both Areas. As seen from the Table 2, Area A applied with normal wash and disinfectants requires 45-55 minutes for cleaning while Area B with Cleaning Solution requires 15-20 minutes only. Thus, a notable amount of water has been saved with Cleaning Solution

TABLE 4

The rating of the cleanliness achieved in Areas A and B

| | Area A With conventional detergent and liquid disinfectant | Area B With Cleaning Solution |
|---|---|---|
| After 1st Rinse of Water | 4 | Not Applied |
| After Spray of actives | 3.2 | 3.2 |
| After 2nd Rinse of Water | 1.7 | 0 |
| After Spray of Disinfectant | 1.3 | Not Required |
| After last Rinse of Water | 0 | Not Required |

Table 5 shows the elimination of odor from both areas. As seen from Table 3, with only one washing, the area treated with the special Cleaning Solution was seen to be free of foul odor. However, when the conventional detergent and liquid disinfectant were used, with multiple rinses the odor was removed only partially.

TABLE 5

The rating of the elimination of odor in Areas A and B

| | Area A With conventional detergent and liquid disinfectant | Area B With Cleaning Solution |
|---|---|---|
| After 1st Rinse of Water | 5 | Not Applied |
| After Spray of actives | 5 | 5 |
| After 2nd Rinse of Water | 3.8 | 0 |
| After Spray of Disinfectant | 3.5 | Not Required |
| After last Rinse of Water | 2.8 | Not Required |

For measuring the amount of disinfection, the areas were tested for the presence of bacteria such as *Salmonella, Escherichia coli, Pseudomonas aeruginosa*. Test showed absence of the bacterial contamination on the swabs from both areas thus showing that both areas are negative of any mentioned bacteria. This shows that both samples eliminated any bacteria.

The experiment provides that the use of cleaning solution has given a convenience, that is, with only one wash, cleanliness, disinfection and odor removing was achieved.

Study 3: Cleaning, Disinfection and Eliminating Odor in a 20 Footer Container Used for Shipping/Transporting Fishes and Other Sea Foods Method Fishes and other Sea Foods are transported or shipped to using a container, where after unloading the cargo, a very foul and fishy odor remains in the container. Before re-using the same container, it needs to be cleaned, disinfected and the foul odor needs to be removed. The entire process has to be safe for humans, fishes/sea creatures and the sea water as well. The product has to be such so as to contain the contamination of the environment. 5% of the Cleaning Solution was used for the analysis For the purpose of the study, three sets of experiment were conducted in different containers. Set 1: washed with water only, Set 2: washed with conventional product, Set 3: washed with the present cleaning solution. The results of washing the container with the present cleaning solution was compared with Set 1 and Set 2.

a) Set 1: Cleaning, disinfecting and odor removing with the Water only.
  i. About 300 Liters of Water was sprayed with a spray gun in Container-1. The process of spraying was repeated 3 times. (as 3 rinses were made with water only)

b) Set 2: Cleaning, disinfecting and odor removing with a conventional product.
  i. Water of about 60-85 Liters was sprayed with a spray gun in Container-2.
  ii. It was followed by spraying Container-2 with a 5% solution of a conventional cleaning product and left for 10 minutes.
  iii. The Container-2 was rinsed with 80-90 Liters of water using spray gun again.
  iv. It was followed by spraying Container-2 again with a 5% solution of the conventional cleaning product and left for another 10 minutes.
  v. Container-2 was rinsed with 100 Liters of water using spray gun.
*Therefore, it was rinsed thrice.

c) Set 3: Cleaning, disinfecting and odor removing with Cleaning Solution.
  i. Water of about 60-85 Liters was sprayed with a spray gun in Container-3.

ii. Cleaning Solution 5.0% was sprayed with a spray gun in Container-3. The solution was retained for 30 minutes.

iii. The Container-3 was rinsed with 75-85 Liters water using spray gun.

*Only two rinse was made. About 90 Liters of water was conserved.

For odor removing, a set of 9 volunteers acted as juries. Rating was done on a scale of 0-5. Five (5) being strongest smell and zero (0) being no smell or odor free.

For disinfecting properties, a $3^{rd}$ party laboratory conducted the analysis by swabbing method after the treatments on Containers.

Results

Table 6 shows the cleanliness and elimination of odor in all three containers. It was observed that Fishy Odor was eliminated in Container-3 with three step process only. The foul odor was removed only partially when the conventional cleaning product were used for Container-2 even after multiple rinses. While on using the cleaning solution, foul odor was completely removed after two rinse. A notable amount of water has been saved with Cleaning Solution.

TABLE 6

The rating of the cleanliness and elimination of odor in all 3 containers

|  | Container-1 With Water only | Container-2 With conventional cleaning product | Container-3 With Cleaning Solution |
|---|---|---|---|
| After $1^{st}$ Rinse of Water | 5 | 5 | 5 |
| After $1^{st}$ Spray of Actives | Not applied | 4.2 | 3.2 |
| After $2^{nd}$ Rinse of Water | 4.8 | 3.7 | 0 |
| After $2^{nd}$ Spray of Actives | Not applied | 3.4 | Not Required |
| After last Rinse of Water | 4.8 | 2.8 | Not Required |

For measuring the amount of disinfection, the swab samples from the areas were tested for the presence of bacteria such as *Salmonella, Escherichia coli, Pseudomonas aeruginosa*. Container-3 test result showed absence of the bacterial contamination on the swabs. Container-2 did not show such disinfection and detectable trace of bacteria remained on the swab.

The Cleaning Solution was most effective in removing/eliminating odor, bacterial contamination and cleaning the surface. The results were achieved in one step whereas with conventional cleaning product the result was achieved in three steps.

What is claimed is:

1. A deodorant formulation, comprising zinc ricinoleate, an amphoteric surfactant which is alkyl polyglucoside derived from C4-C18 alcohol, a nonionic surfactant, an antimicrobial agent and water.

2. The deodorant formulation according to claim 1, wherein the formulation comprises zinc ricinoleate in an amount of from 1 to 60% by weight.

3. The deodorant formulation according to claim 1, wherein the formulation comprises the amphoteric surfactant in an amount of from 1 to 25% by weight.

4. The deodorant formulation according to claim 1, wherein the formulation comprises the nonionic surfactant in an amount of from 1 to 60% by weight.

5. The deodorant formulation according to claim 1, wherein the formulation comprises the antimicrobial agent in an amount of from 1 to 25% by weight.

6. The deodorant formulation according to claim 1, wherein the formulation comprises water in an amount of from 1 to 95% by weight.

7. The deodorant formulation according to claim 1, wherein the amphoteric surfactant is selected from betaines and sultaines.

8. The deodorant formulation according to claim 7, wherein the amphoteric surfactant is Cocoamido propyl betaine or Cocodiamido propyl hydroxyl sultaine.

9. The deodorant formulation as claimed in claim 1, the wherein the alkyl polyglucoside is derived from C6 to C14 alcohol.

10. The deodorant formulation as claimed in claim 1, wherein the antimicrobial agent is selectively alkyl dimethyl benzyl ammonium chloride.

11. The deodorant formulation as claimed in claim 10, wherein the alkyl dimethyl benzyl ammonium chloride acts a preservative, surfactant and as well as a disinfecting agent.

12. A deodorant formulation comprising zinc ricinoleate in an amount of 20% by weight, Cocoamido propyl betaine or Cocodiamido propyl hydroxyl sultaine in an amount of 10% by weight, alkyl poly glucoside in an amount of 40% by weight, alkyl dimethyl benzyl ammonium chloride in an amount of 10% by weight, and water in an amount of 20% by weight.

13. A process for preparing deodorant formulation, comprising the steps of:
    a. adding nonionic surfactant which is alkyl polyglucoside derived from C4-C18 alcohol to water at room temperature, mixing well and adding Zn-ricinoleate to obtain a homogenous mixture;
    b. adding antimicrobial agent, and amphoteric surfactant to the homogenous mixture, to obtain the deodorant formulation.

14. A process for preparing deodorant formulation, comprising the steps of:
    a. adding alkyl poly glucoside in an amount of 40% by weight to water in an amount of 20% by weight at room temperature, mixing well and adding zinc ricinoleate in an amount of 20% by weight to obtain a homogenous mixture;
    b. adding alkyl dimethyl benzyl ammonium chloride in an amount of 10% by weight, and Cocoamido propyl betaine or Cocodiamido propyl hydroxyl sultaine in an amount of 10% by weight to the homogenous mixture, to obtain the deodorant formulation.

* * * * *